US00PP35753P2

(12) United States Plant Patent
Westervelt et al.

(10) Patent No.: US PP35,753 P2
(45) Date of Patent: Apr. 16, 2024

(54) ***GINKGO* TREE NAMED 'WACONDA GOLD'**

(50) Latin Name: *Ginkgo biloba*
Varietal Denomination: Waconda Gold

(71) Applicants: Keith D. Westervelt, Manhattan, KS (US); James A. Ord, Manhattan, KS (US)

(72) Inventors: Keith D. Westervelt, Manhattan, KS (US); James A. Ord, Manhattan, KS (US)

( * ) Notice: Subject to any disclaimer, the term of this patent is extended or adjusted under 35 U.S.C. 154(b) by 220 days.

(21) Appl. No.: 17/874,245

(22) Filed: Jul. 26, 2022

(51) Int. Cl.
*A01H 7/00* (2006.01)

(52) U.S. Cl.
USPC ..... Plt./216

(58) Field of Classification Search
USPC ..... Plt./216, 213
CPC ..... A01H 7/00; A01H 5/00
See application file for complete search history.

(56) References Cited

PUBLICATIONS

Sacrament Tree Foundation 'Autumn Gold' *Ginkgo*, retrieved on Sep. 1, 2022 https://sactree.org/trees/autumn-gold-ginkgo/, 3 pp. (Year: 2022).*

* cited by examiner

*Primary Examiner* — June Hwu
(74) *Attorney, Agent, or Firm* — Penny J Aguirre

(57) ABSTRACT

A new cultivar of *Ginkgo* tree named 'Waconda Gold' that is characterized by its very uniform growth habit and shape, its upright ascending branches and a pyramidal plant habit, its healthy foliage that is dark green in color, its strong central leader, and its good growth rate.

3 Drawing Sheets

Botanical classification: *Ginkgo biloba*.
Variety denomination: 'Waconda Gold'.

BACKGROUND OF THE INVENTION

The present invention relates to a new and distinct cultivar of *Ginkgo biloba* and will be referred to hereafter by its cultivar name, 'Waconda Gold'. 'Waconda Gold' is a new cultivar of *Ginkgo* tree grown for use as a landscape plant.

The Inventors discovered the new cultivar, 'Waconda Gold' as a chance seedling that was growing at a residence in Glen Elder, Kans. in June of 2008. The parents are therefore unknown.

Asexual propagation of the new cultivar was first accomplished by grafting under the direction of the Inventors in Amity, Oreg. in January of 2018. Asexual propagation of the new cultivar by grafting has been determined that the characteristics are stable and are reproduced true to type in successive generations.

SUMMARY OF THE INVENTION

The following traits have been repeatedly observed and represent the characteristics of the new cultivar, which in combination distinguish 'Waconda Gold' as a new distinct cultivar of *Ginkgo*.

1. 'Waconda Gold' exhibits a very uniform growth habit.
2. 'Waconda Gold' exhibits upright ascending branches and a pyramidal plant habit.
3. 'Waconda Gold' exhibits healthy foliage that is dark green in color.
4. 'Waconda Gold' exhibits a strong central leader.
5. 'Waconda Gold' exhibits a good growth rate.

'Waconda Gold' can be most closely compared to the cultivars 'Autumn Gold' (not patented) and 'Magyar' (not patented). 'Autumn Gold' is similar to 'Waconda Gold' in having healthy foliage that is gold in color in fall. 'Autumn Gold' differs from 'Waconda Gold' in having leaves that are light green in color, a less uniform branching habit, a slower growth rate, and in lacking a strong central leader. 'Magyar' is similar to 'Waconda Gold' in having a strong and uniform branching habit and gold color foliage in the fall. 'Magyar' is similar to 'Waconda Gold' in having healthy foliage that is gold in color in fall. 'Magyar' differs from 'Waconda Gold' in having leaves that are lighter green in color and a slower growth rate, and in lacking a strong central leader.

BRIEF DESCRIPTION OF THE DRAWINGS

The accompanying color photographs illustrate the overall appearance and distinct characteristics of the new *Gingko*. The photographs were taken of the original 14-year-old tree of 'Waconda Gold' as growing in the landscape in Glen Elder, Kans.

The photograph in FIG. 1 provides a view of the plant habit of 'Waconda Gold'.

Figure 1:
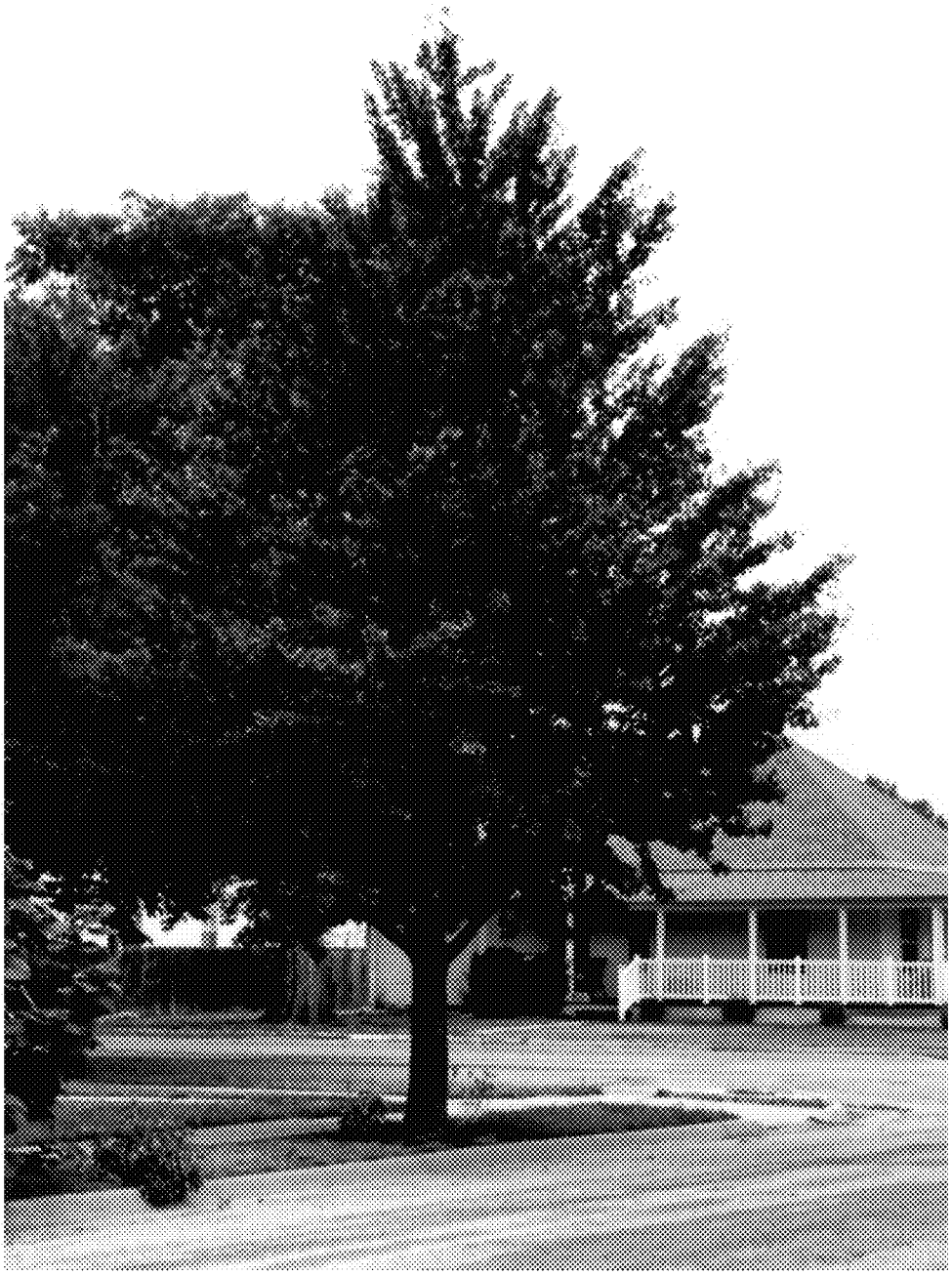
Figure 2:
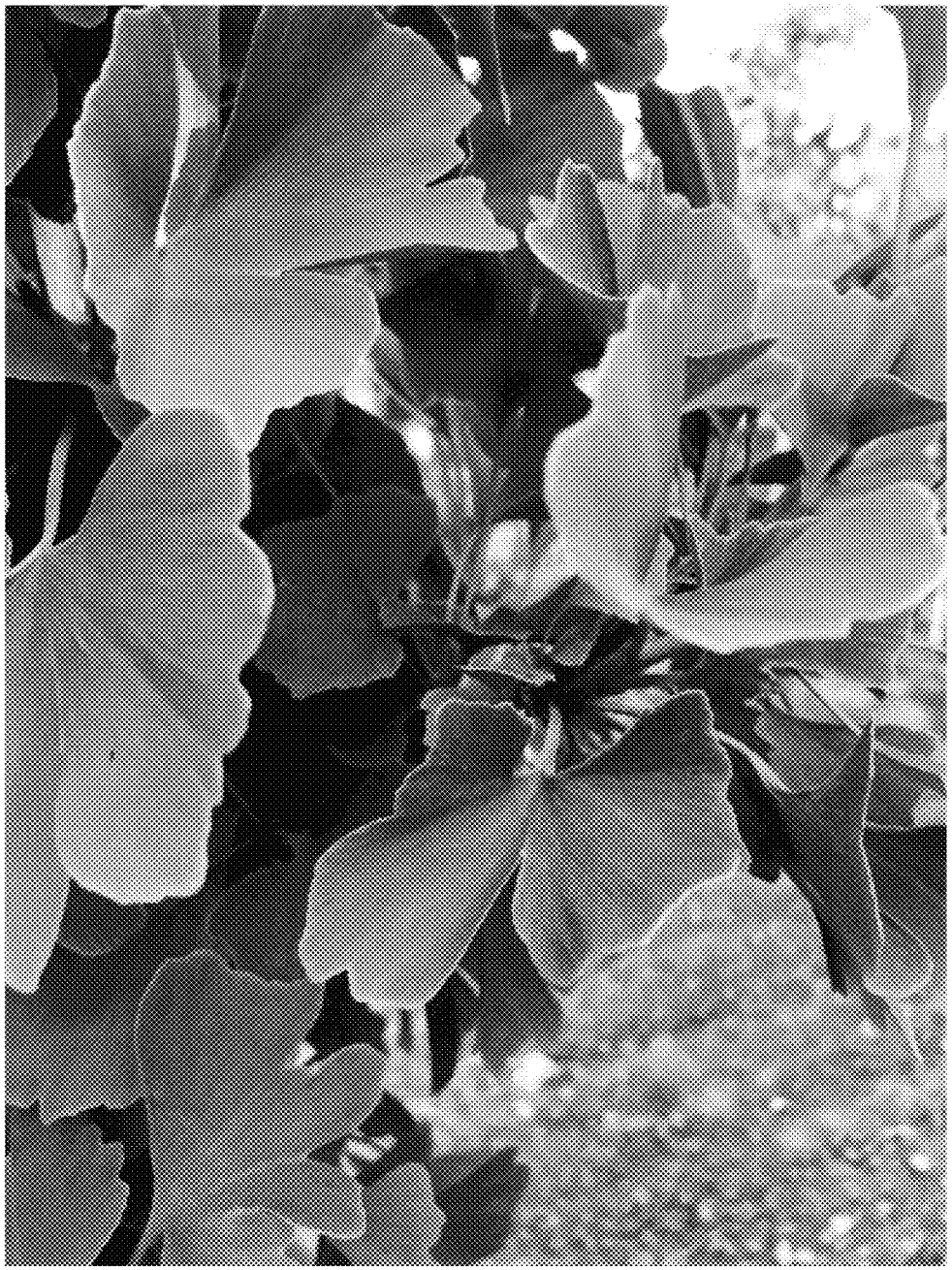

The photograph in FIG. 2 provides a close-up view of the foliage of 'Waconda Gold'.

Figure 3:
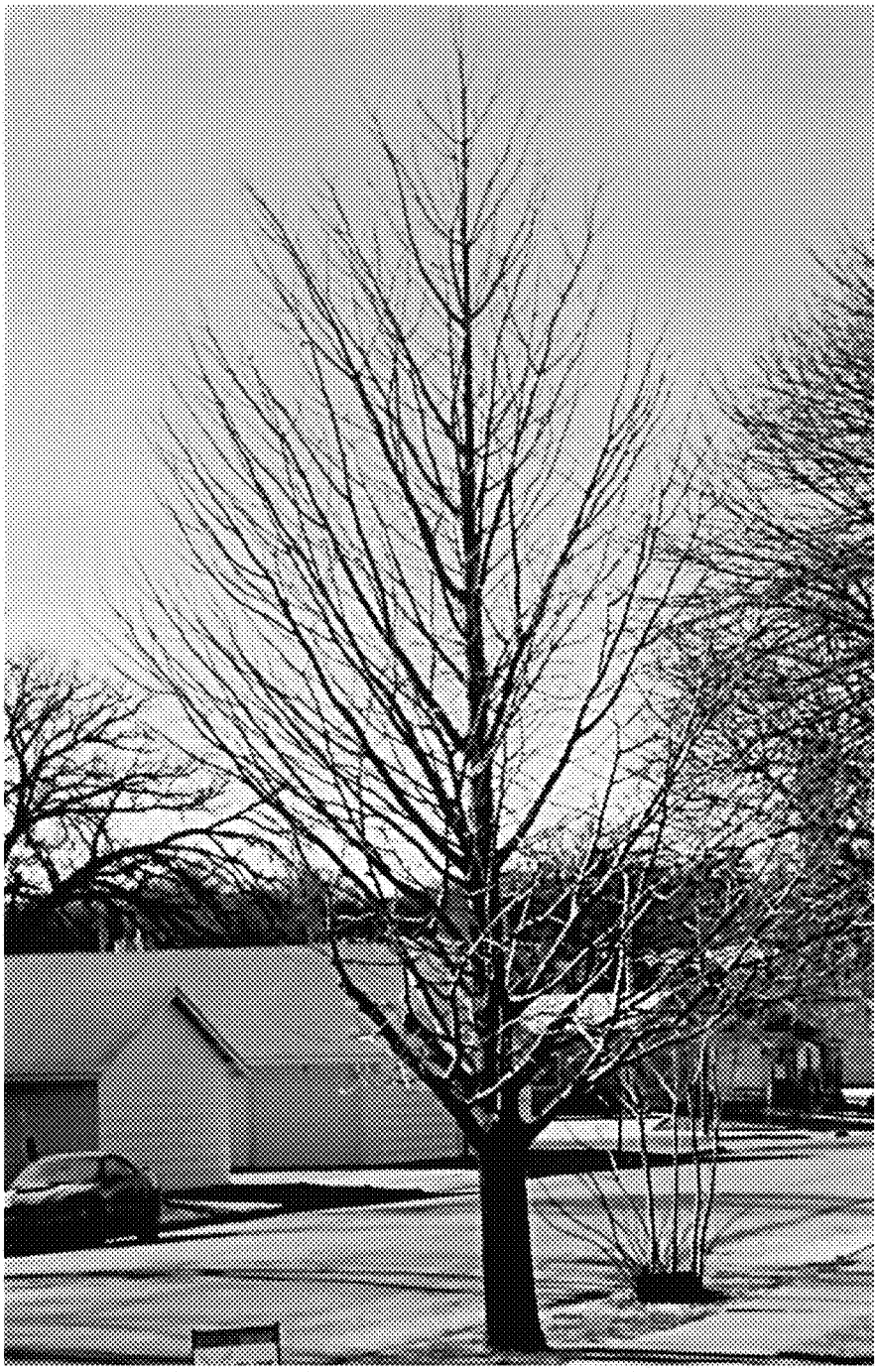

The photograph in FIG. 3 provides a view of the branching of 'Waconda Gold' when dormant.

The colors in the photograph are as close as possible with the digital photography techniques available, the color values cited in the detailed botanical description accurately describe the colors of the new *Ginkgo*.

DETAILED BOTANICAL DESCRIPTION

The following is a detailed description of 3 year-old trees of the new cultivar as grown outdoors in 5-gallon containers in Amity, Oreg. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Plant type*.—Deciduous tree.

*Plant habit*.—Upright, uniform, and pyramidal.

*Height and spread*.—Average of 1.4 m in height, 1.5 cm in diameter, up to 6 m in height and 12.2 m in width when mature in the landscape.

*Hardiness*.—At least in U.S.D.A. Zone 6.

*Diseases and pests*.—Have been observed to be disease free (typical for plants of *Ginkgo biloba*) however no specific resistance to any disease has been identified, no resistance or susceptibility to pests has been observed.

*Root description*.—Fibrous, freely branched, 199A and 199B in color.

*Propagation*.—Grafting.

*Root development*.—6 to 8 weeks for a graft to take after grafting onto *Ginkgo biloba* rootstock.

*Growth rate*.—Moderate but vigorous for typical plants of *Ginkgo biloba*.

Stem description:

*Shape*.—Rounded.

*Stem color*.—Branches and young bark; Streaks of N199A and 196A, mature bark; ridges of N199A over 199D.

*Stem size*.—Average of 1.4 m in length and 1.5 cm in diameter.

*Stem surface*.—Branches and young bark; finely ridged, Mature bark; rugose, slightly exfoliating, matte and dry.

*Stem strength*.—Very strong.

*Branching habit*.—1 main branch, uniform branching with ascending branches.

Foliage description:

*Leaf shape*.—Flabellate and slightly convex.

*Leaf division*.—Simple.

*Leaf base*.—Cordate.

*Leaf apex*.—Cleft; 1 to 3 notches, 5 mm to 1.2 cm in depth.

*Leaf fragrance*.—None.

*Leaf venation*.—Open dichotomous, upper and lower surface in the sun; 144A, upper and lower surface in the shade; color matches leaf surface color.

*Leaf margins*.—Entire, undulate.

*Leaf arrangement*.—Alternate, whorled.

*Leaf attachment*.—Petiolate.

*Leaf buds*.—Bluntly deltoid to broadly conical in shape, matte, an average 7 mm in length and 5 mm in diameter, color; 164A and 145A.

*Leaf surface*.—Both surfaces glabrous and slightly glossy.

*Leaf size*.—Average of 2.5 cm in length and 4 cm in width.

*Leaf color*.—New growth; a blend of 144A and N144B, mature leaves; a blend of 137A and 189A, fall color; primarily 11A.

*Petioles*.—Flattened in shape, average of 1 cm in length, 1 mm in width, color; 144A and N144B.

Flower, fruit, and seed description: Has not been observed to date.

It is claimed:

1. A new and distinct cultivar of *Ginkgo* tree named 'Waconda Gold' as herein illustrated and described.

* * * * *